United States Patent [19]

Hohmann et al.

[11] 4,259,248

[45] Mar. 31, 1981

[54] PROCESS FOR THE PREPARATION OF MIXTURES OF DINITROANTHRAQUINONES WITH A HIGH CONTENT OF 1,5- AND 1,8- DINITROANTHRAQUINONE

[75] Inventors: Walter Hohmann; Klaus Wunderlich, both of Leverkusen, Fed. Rep. of Germany

[73] Assignee: Bayer Aktiengesellschaft, Leverkusen, Fed. Rep. of Germany

[21] Appl. No.: 49,708

[22] Filed: Jun. 18, 1979

Related U.S. Application Data

[63] Continuation of Ser. No. 825,002, Aug. 16, 1977, abandoned.

[30] Foreign Application Priority Data

Aug. 21, 1976 [DE] Fed. Rep. of Germany ....... 2637732

[51] Int. Cl.$^3$ .............................................. C07C 97/12
[52] U.S. Cl. .................................................. 260/369
[58] Field of Search ........................................ 260/369

[56] References Cited

U.S. PATENT DOCUMENTS

| | | | |
|---|---|---|---|
| 3,818,052 | 6/1974 | Hohmann et al. | 260/369 |
| 3,963,762 | 6/1976 | Hohmann | 260/369 |

OTHER PUBLICATIONS

*Chemical Abstracts*, vol. 26, Jan.–Mar. 1932, p. 1278, Eugeh Heffi "Dinitroanthraquinone".
Anthracene and Anthraquinone, Barnett, E. de Barry; O. Van Nostrand Co., New York, 1925, p. 167.

*Primary Examiner*—Patrick Garvin
*Assistant Examiner*—Raymond K. Covington

[57] ABSTRACT

A process has been developed for the preparation of mixtures of dinitroanthraquinones with a high content of 1,5- and 1,8- dinitroanthraquinone by nitration with nitric acid in the presence of sulphuric acid with heating wherein anthraquinone, 1-nitroanthraquinone or a mixture of them is treated with about 1.5 to about 2.5 times the amount by weight of nitric acid, relative to the feed material, in the presence of about 0.75 times to twice the amount by weight, relative to nitric acid, of sulphuric acid, the temperature first being kept in the range from room temperature to about 50° C. until at least 50% of the starting material or materials has been dinitrated, then adjusting the temperature to about 50° C. to about 70° C. to complete the dinitration.

8 Claims, No Drawings

PROCESS FOR THE PREPARATION OF MIXTURES OF DINITROANTHRAQUINONES WITH A HIGH CONTENT OF 1,5- AND 1,8-DINITROANTHRAQUINONE

This is a continuation of application Ser. No. 825,002, filed 8/16/77, now abandoned.

The present invention relates to a process for the preparation of mixtures of dinitroanthraquinones with a high content of 1,5- and 1,8-dinitroanthraquinone.

It is known to prepare dinitroanthraquinone by dinitration of anthraquinone in excess nitric acid or with nitric acid/sulphuric acid mixtures under specific reaction conditions. Thus, for example, the following processes have been described a process in which the mixed acid (mixture of nitric acid and sulphuric acid) is added dropwise to anthraquinone in 100% strength sulphuric acid and the mixture is heated to 80° C. for 5 hours or to 125° C. for 2 hours (Helv. chim. Acta, 14, 1404 (1931)), a process in which heating to 95° C. is carried out for 2 hours in 96% strength sulphuric acid using mixed acid (U.S. Pat. No. 2,607,782), a process in which anthraquinone is dissolved in 10 times the amount of sulphuric acid monohydrate and the solution is treated with nitrating acid at room temperature (Houben-Weyl, Methoden der organischen Chemie (Methods of Organic Chemistry), 4th edition (1971), Stuttgart, volume X/1, page 615), a process in which either the anthraquinone is gradually added at 5° C. to a mixture of 98.5% strength nitric acid and 100% strength sulphuric acid and the mixture is stirred at this temperature for 3 hours, or the anthraquinone is dissolved in 98.8% strength nitric acid and 100% strength sulphuric acid is added dropwise at 5° to 10° C. and the mixture is stirred at 10° to 15° C. for 3 hours (DT-OS (German Published Specification No.) 2,248,704) and a process in which nitric acid is metered slowly into a suspension of anthraquinone in 75–94% strength by weight sulphuric acid at temperatures between 10° and 40° C. or 45° and 48° C. without the temperature exceeding 100° C. (DT-OS (German Published Specification No.) 2,459,164).

A disadvantage of these processes is the use of large amounts of nitric acid and sulphuric acid, which have to be worked up at high cost, which is an increased burden on the economy of the processes. In addition, with some of the processes mentioned large amounts of $\alpha,\beta$-dinitroanthraquinone and $\beta,\beta$-dinitroanthraquinone, that is to say 1,6-, 1,7-, 2,6- or 2,7-dinitroanthraquinone, which are not valuable as intermediate products for dyestuffs, are formed so that, overall, a poor yield for 1,5- and 1,8-dinitroanthraquinone results.

A process for the preparation of mixtures of dinitroanthraquinones with a high content of 1,5- and 1,8-dinitroanthraquinone by nitration with nitric acid in the presence of sulphuric acid with heating has now been found, which is characterised in that anthraquinone and/or 1-nitroanthraquinone, which may contain impurities, is treated with about 1.5 to 2.5 times the amount by weight of nitric acid, relative to the feed material in the presence of about 0.75 times to twice the amount by weight, relative to nitric acid, of sulphuric acid, the temperature first being kept in the range from room temperature to about 50° C. until at least 50% of the anthraquinone and/or of the 1-nitroanthraquinone, which may contain impurities, has been dinitrated and the temperature then being adjusted to about 50° to 70° C.

Using the process according to the invention, it is possible to convert anthraquinone and/or 1-nitroanthraquinone, which may contain impurities, into dinitroanthraquinones in a 95 to 100% yield. When anthraquinone is employed, the resulting mixture of dinitroanthraquinones as a rule contains about 74 to 80% by weight of 1,5- and 1,8-dinitroanthraquinone, the ratio of 1,5-dinitroanthraquinone to 1,8-dinitroanthraquinone, between themselves, being about 1.05:1 to 1.15:1. The yield of 1,5- and 1,8-dinitroanthraquinone, relative to anthraquinone, is between about 74% and 78% of the yield calculated from the reaction equation.

The process according to the invention can, for example, be carried out by introducing the anthraquinone and/or the 1-nitroanthraquinone, which may contain impurities, into a mixture of nitric acid and sulphuric acid, at about 20° to 40° C., whilst stirring. After at least half of the material employed has been dinitrated, which usually has taken place after the introduction of the feed material has ended, the temperature is raised to about 50° to 70° C. In this way it is possible again to accelerate the reaction, which greatly slows down towards the end; this means that the reaction time is shortened without a significant increase in the content of $\alpha,\beta$-dinitroanthraquinone in the mixture of dinitroanthraquinones taking place. The reaction mixture is kept at the desired reaction temperature until anthraquinone and nitroanthraquinone have disappeared or can be detected only in insignificant amounts. After the reaction has ended, the mixture is cooled if necessary and stirred into water or ice water and the product which precipitates is filtered off, washed until neutral and then dried. The yield of the mixture of dinitroanthraquinones is about 95% to 100%, relatively to anthraquinone, of the yield calculated from the reaction equation.

In addition to the discontinuous procedure described above, the process according to the invention is especially suitable for fully continuous operation, in which case suitable reactors which can be used are, for example, a tubular reactor or a multi-stage reaction cascade. Thus, a 3 to 4-stage reaction cascade has proved to be particularly suitable. In this case the anthraquinone and/or the 1-nitroanthraquinone, which may contain impurities, and the mixed acid (nitric acid/sulphuric acid) are continuously metered into the first cascade stage at temperatures of from about room temperature to about 40° C., whilst in the following stages the temperature is then raised stepwise, by about 5° to 10° C. in each case. Continuous dilution with water is then effected at temperatures of about 30° to about 80° C. in a dilution vessel. The overflow from the dilution vessel is filtered and the residue is washed until neutral and dried. It is also possible to carry out the dilution with the wash filtrate obtained after the wash, instead of with water. With the continuous procedure described, the total residence time is about ½ to 3 hours.

The yield of crude mixture of dinitroanthraquinones is about 95° to 100° C., relative to anthraquinone, of the yield calculated from the reaction equation.

Both anthraquinone and 1-nitroanthraquinone and mixtures of anthraquinone and 1-nitroanthraquinone can be employed in the process according to the invention. However, it is also possible to employ 1-nitroanthraquinone, which contains impurities, such as that obtained, for example, from the processes described in DT-OS (German Published Specification No.) 2,233,185 and DT-OS (German Published Specification No.) 2,256,644, both on its own and as a mixture with anthraquinone. Depending on whether the substances used are residues from crystallisation of the mother liquor which are obtained from the purification of 1-nitroanthraquinone or distillation residues from the distillation of 1-nitroanthraquinone, the mixtures also contain, in addition to 1-nitroanthraquinone, anthraquinone and 2-nitroanthraquinone as well as various dinitroanthraquinones, which, however, remain unchanged during the dinitration. Because of their relatively high content of 2-nitroanthraquinone and/or α,β-dinitroanthraquinone, the use of residues from the crystallisation of the mother liquor leads to higher α,β- and β,β-dinitroanthraquinone contents in the mixture of dinitroanthraquinones which is obtained according to the invention. When distillation residues are employed, it is possible for higher α,α-dinitroanthraquinone contents to arise in the mixture of dinitroanthraquinones which is obtained according to the invention, due to the relatively high contents of 1-nitroanthraquinone and α,α-dinitroanthraquinone in the particular material.

In this case the yield of 1,5- and 1,8-dinitroanthraquinone, relative to anthraquinone employed, is about 73 to 87% of theory, relative to the sum of the anthraquinone and 1-nitroanthraquinone employed. However, the yield can also rise considerably above 80% of theory and, with a small proportion of anthraquinone but a high proportion of 1-nitroanthraquinone, as in Example 15, can reach about 90%.

About 85 to 100% strength by weight, preferably about 90 to 100% strength and particularly preferentially about 96% strength by weight sulphuric acid is used as the reaction medium. The amount of sulphuric acid added is generally so measured that the sulphuric acid is present in an amount by weight which is about 0.75 times to twice the amount by weight of nitric acid. Preferably, the sulphuric acid is added in an amount by weight which is 1.0 to 1.5 times that of nitric acid.

The nitration requires about 1.5 to 2.5 times the amount by weight of nitric acid, relative to anthraquinone and/or 1-nitroanthraquinone, which may contain impurities. Preferably, about 1.7 to 2.4 times the amount by weight of nitric acid is used.

A suitable nitric acid is highly concentrated nitric acid with contents of about 96 to 100% by weight and the use of an about 98% strength by weight nitric acid has proved to be particularly appropriate.

The process according to the invention is generally carried out at temperatures of from about room temperature to about 70° C.; however, it is necessary that the temperature is raised above about 50° C. only when at least 50% of the anthraquinone and/or of the 1-nitroanthraquinone, which may contain impurities, has been dinitrated, since, otherwise, a distinct reduction in the α,α'-dinitroanthraquinone content of the end product takes place. Since, in an industrial process, rapid removal of heat at temperature below 30° C. is very expensive, the procedure employed is advantageously such that the nitration is first started at about 30° to 40° C. and the temperature is then adjusted to the range of about 50° C. to 70° C. after at least 50% of the anthraquinone and/or of the 1-nitroanthraquinone, which may contain impurities, employed are in the form of dinitroanthraquinones.

The reaction mixture can be worked up, for example, by separating off the resulting mixture of dinitroanthraquinones from the reaction mixture by filtering or centrifuging, washing with water until neutral and, if required, drying.

The process according to the invention gives a mixture of dinitroanthraquinones which has a content of 1,5-dinitroanthraquinone and 1,8-dinitroanthraquinone which is between about 38 and 41% of theory (for 1,5-dinitroanthraquinone) and about 34 and 37% of theory (for 1,8-dinitroanthraquinone), in yields of between about 74 and 80% of theory, relative to the anthraquinone employed.

In addition to the high space-time yield of the mixture of dinitroanthraquinones which has a high content of 1,5- and 1,8-dinitroanthraquinone, the process according to the invention has yet further advantages over the processes of the state of the art. Thus, with the process according to the invention, the otherwise customary use of large amounts of nitric acid and/or sulphuric acid, which, after the nitration, have to be worked up at high cost in order to re-use them, if necessary, for a further nitration, is avoided. Furthermore, the process according to the present invention prevents the formation of larger amounts of α,β- and β,β-dinitroanthraquinones, which are not valuable as intermediate products for dyestuffs and would adversely effect the further processing of the 1,5- and 1,8-dinitroanthraquinones to dyestuffs.

The mixtures of dinitroanthraquinones with a high content of 1,5- and 1,8-dinitroanthraquinone which are prepared by the process according to the invention are separated into the 1,5- and 1,8-dinitroanthraquinone isomers, the isomers are converted into the corresponding amino compounds and the latter are then further processed to anthraquinone dyestuffs (see, for example, Friedlaender Fortschritte der Teerfarben-Fabrikation (Advances in the Production of Coal-tar Dyes), part 22 (1935), page 1014 and Fiat Final Report 1313, German Dyestuffs and Intermediates, II, page 26).

The examples which follow are intended further to describe the process according to the invention without restricting it to these examples. The temperatures indicated in the examples denote degrees Centigrade and the percentage data for the acids are by weight.

EXAMPLE 1

208 g of anthraquinone are introduced into a mixed acid consisting of 458 g of 96% strength sulphuric acid and 424 g of 98% strength nitric acid in the course of 15 minutes, at 40° C., whilst cooling. After stirring at 40° for a further 15 minutes, the mixture is stirred for a further ½ hour at 50° C. After stirring the mixture into 3,000 g of ice water and filtering off the product which has precipitated, washing it until neutral and drying, 293 g (93.3%) of a mixture of dinitroanthraquinones which has the following composition is obtained:

| Analysis: | |
|---|---|
| 2,6-Dinitroanthraquinone | 0.44% |
| 2,7-Dinitroanthraquinone | 0.48% |
| 1-Nitroanthraquinone | 2.19% |
| 1,6-Dinitroanthraquinone | 9.22% |
| 1,7-Dinitroanthraquinone | 9.29% |
| 1,5-Dinitroanthraquinone | 38.4% (37.8% of theory) |
| 1,8-Dinitroanthraquinone | 35.2% (34.6% of theory) |
| Anthraquinone | 0.13% |

EXAMPLE 2

If the procedure followed is as described in Example 1 and, after stirring for ½ an hour at 50° C., the mixture is stirred for a further ½ hour at 60° C., the working up described above gives 293 g (98.3%) of a mixture of dinitroanthraquinones which has the following composition:

| Analysis: | |
|---|---|
| 2,6-Dinitroanthraquinone | 0.42% |
| 2,7-Dinitroanthraquinone | 0.44% |
| 1-Nitroanthraquinone | 0.60% |
| 1,6-Dinitroanthraquinone | 9.24% |
| 1,7-Dinitroanthraquinone | 9.08% |
| 1,5-Dinitroanthraquinone | 39.6% (39.0% of theory) |
| 1,8-Dinitroanthraquinone | 34.5% (33.8% of theory) |
| Anthraquinone | 0.09% |

EXAMPLE 3

416 g of sulphuric acid monohydrate (100% strength sulphuric acid) are allowed to run slowly into 566 g of nitric acid (98% strength), whilst cooling well. 232.5 g of anthraquinone are then introduced in the course of about ½ an hour, at 20° to 40°, while cooling. The mixture is then warmed to 40° and after ½ an hour the temperature is raised to 50°. After stirring for ½ an hour at 50°, the mixture is cooled to 35° to 40° and stirred into 3,000 g of ice water. The product which has fallen on is filtered off, washed until neutral and dried at 100° C. This gives 330 g (99%) of a mixture of dinitroanthraquinones which has the following composition:

| Analysis: | |
|---|---|
| 2,6-Dinitroanthraquinone | 0.34% |
| 2,7-Dinitroanthraquinone | 0.43% |
| 1-Nitroanthraquinone | 0.47% |
| 1,6-Dinitroanthraquinone | 8.98% |
| 1,7-Dinitroanthraquinone | 8.89% |
| 1,5-Dinitroanthraquinone | 40.6% (40.2% of theory) |
| 1,8-Dinitroanthraquinone | 37.2% (36.8% of theory) |

EXAMPLE 4

Per hour, 416 g of anthraquinone and 1,625 g of a mixed acid which consists of 48.0% of nitric acid and 48.5% of sulphuric acid and has been prepared by stirring 47.7 g of 96% strength sulphuric acid into 46.7 kg of 98% strength nitric acid, whilst cooling, are metered continuously, at 40°, into the first reaction vessel of a three-stage reaction cascade consisting of three reaction vessels, each of 500 ml capacity, provided with stirrers and a thermometer and a downstream 500 ml dilution vessel. The temperature is adjusted to 50° in the second reaction vessel and to 60° in the third reaction vessel. Continuous dilution with 2,300 ml of water per hour takes place at 60° in the dilution vessel. The overflow from the dilution vessel is filtered and the residue is washed until neutral. It is also possible to feed the dilution vessel with the acid wash filtrate which is obtained after a wash with 2,000 ml of water, instead of with water.

After drying, 588 g (98.5%) of a mixture of dinitroanthraquinones which has the following average composition are obtained per hour:

| Analysis: | |
|---|---|
| 2,6-Dinitroanthraquinone | 0.52% |
| 2,7-Dinitroanthraquinone | 0.45% |
| 1-Nitroanthraquinone | 1.78% |
| 1,6-Dinitroanthraquinone | 9.50% |
| 1,7-Dinitroanthraquinone | 9.24% |
| 1,5-Dinitroanthraquinone | 38.50% (37.9% of theory) |
| 1,8-Dinitroanthraquinone | 35.9% (35.4% of theory) |

After working up, the samples taken from the individual reaction vessels showed the following compositions:

| Reaction vessel | 1. (40°) | 2. (50°) | 3. (60°) |
|---|---|---|---|
| 2,6-Dinitroanthraquinone | 0.38% | 0.40% | 0.40% |
| 2,7-Dinitroanthraquinone | 0.33% | 0.35% | 0.38% |
| 1-Nitroanthraquinone | 4.07% | 2.70% | 1.86% |
| 1,6-Dinitroanthraquinone | 9.43% | 9.53% | 9.81% |
| 1,7-Dinitroanthraquinone | 9.39% | 9.50% | 9.51% |
| 1,5-Dinitroanthraquinone | 37.0% | 37.6% | 38.3% |
| 1,8-Dinitroanthraquinone | 34.5% | 35.3% | 35.7% |
| Anthraquinone | 0.91% | 0.1% | 0.1% |
| 2-Nitroanthraquinone | 0.10% | — | — |

EXAMPLE 5

164.2 g of a mixture of 73.4 g of anthraquinone, 56.7 g of the product obtained from the mother liquor from the purification of 1-nitroanthraquinone and 34.1 g of a distillation residue which has been obtained from the distillation of 1-nitroanthraquinone and has the following composition: 48.4% of anthraquinone, 5.5% of 1,5-dinitroanthraquinone, 5.1% of 1,8-dinitroanthraquinone, 1.5% of 1,7-dinitroanthraquinone, 26% of 1-nitroanthraquinone and 9.1% of 2-nitroanthraquinone, are introduced, at 20° to 30°, in the course of 25 minutes, into a mixture of 340 g of 98% strength nitric acid and 513 g of 96% strength sulphuric acid. The mixture is then stirred for ½ an hour at 40° and for 4½ hours at 50°. After working up in accordance with the procedure indicated in Example 1, 199 g (95.8%) of a mixture of dinitroanthraquinones which has the following composition are obtained:

| Analysis: | |
|---|---|
| 1-Nitroanthraquinone | 0.7% |
| 1,6-Dinitroanthraquinone | 11.0% |
| 1,7-Dinitroanthraquinone | 11.1% |
| 1,5-Dinitroanthraquinone | 38.2% (40.7% of theory)[x] |
| 1,8-Dinitroanthraquinone | 33.0% (34.9% of theory) |
| 2,6-Dinitroanthraquinone | 0.56% |
| 2,7-Dinitroanthraquinone | 0.57% |

[x]Calculation: The theoretical yield from Σanthraquinone and 1-nitroanthraquinone related to 1,5- and 1,8-dinitroanthraquinone formed (= total 1,5-dinitroanthraquinone and 1,8-dinitroanthraquinone to 1,5-dinitroanthraquinone and 1,8-dinitroanthraquinone employed).

After working up, the 1-nitroanthraquinone content of a sample taken after introduction of the mixture was 10%, after ½ an hour at 40° was 5 to 7% and after 2 hours at 50° was 1% (semi-quantitative analysis).

EXAMPLE 6

126 g of anthraquinone are introduced in the course of 15 minutes, at 38° to 42°, into 233.5 g of 98% strength nitric acid and 238.5 g of 96% strength sulphuric acid, whilst stirring and cooling. Calculated after ½ an hour from the start of the introduction, the mixture is stirred for ½ an hour at 50° and for ½ an hour at 60°. It is then diluted, at 50° to 60°, with 673 ml of water and the product which has precipitated is filtered off at 50° and washed with water until neutral. After drying, 178.2 g (98.8%) of a mixture of dinitroanthraquinones which has the following composition are obtained:

| Analysis: | |
|---|---|
| 2,6-Dinitroanthraquinone | 0.46% |
| 2,7-Dinitroanthraquinone | 0.42% |
| 1,6-Dinitroanthraquinone | 9.72% |
| 1,7-Dinitroanthraquinone | 9.52% |
| 1,5-Dinitroanthraquinone | 40.10% (39.6% of theory) |
| 1,8-Dinitroanthraquinone | 35.50% (35.1% of theory) |
| 1-Nitroanthraquinone | 0.66% |

EXAMPLE 7

The procedure is as in Example 6 but the anthraquinone is introduced at 30° and the nitration is carried out at 40° (½ an hour) and then brought to completion at 70° (¾ an hour). This gives 178.5 g (98.9%) of a mixture of dinitroanthraquinones which has the following composition:

| Analysis: | |
|---|---|
| 2,6-Dinitroanthraquinone | 0.38% |
| 2,7-Dinitroanthraquinone | 0.35% |
| 1,6-Dinitroanthraquinone | 8.93% |
| 1,7-Dinitroanthraquinone | 8.77% |
| 1,5-Dinitroanthraquinone | 40.90% (40.5% of theory) |
| 1,8-Dinitroanthraquinone | 36.60% (36.2% of theory) |
| 1-Nitroanthraquinone | 0.72% |

EXAMPLE 8

116 g of anthraquinone are introduced, at 38° to 42°, in the course of ¼ hour into 215 g of 98% strength nitric acid and 241 g of 96% strength sulphuric acid. After a further ¼ hour at 40°, the mixture is stirred for a further ½ hour at 50° and a further ½ hour at 60°. The mixture is then introduced into 1,500 g of ice water and the product is filtered off, washed until neutral and dried. This gives 165 g (99.2%) of a mixture of dinitroanthraquinones which has the following composition:

| 2,6-Dinitroanthraquinone | 0.31% |
|---|---|
| 2,7-Dinitroanthraquinone | 0.32% |
| 1,6-Dinitroanthraquinone | 9.39% |
| 1,7-Dinitroanthraquinone | 9.46% |
| 1,5-Dinitroanthraquinone | 41.00% (= 40.7% of theory) |
| 1,8-Dinitroanthraquinone | 36.50% (= 36.2% of theory) |
| 1-Nitroanthraquinone | 1.05% |

EXAMPLE 9

420 g of a mixture of 188 g of anthraquinone, 145 g of the product obtained from the mother liquor from the prepurification of 1-nitroanthraquinone and 87 g of a distillation residue which has been obtained from the distillation of 1-nitroanthraquinone and has the following composition: 48.4% of anthraquinone, 5.5% of 1,5-dinitroanthraquinone, 5.1% of 1,8-dinitroanthraquinone, 1.5% of 1,7-dinitroanthraquinone and 1.4% of 1,6-dinitroanthraquinone, 26.7% of 1-nitroanthraquinone and 9.1% of 2-nitroanthraquinone, are introduced, at 38° to 40°, in the course of ¼ hour, into 627 g of 98% strength nitric acid and 702 g of 96% strength sulphuric acid. After further stirring (¼ hour) at 40°, the mixture is warmed to 50° for ½ an hour and to 60° for ½ an hour. The mixture is then introduced into 3,000 g of ice water and the product which has precipitated is filtered off, washed until neutral and dried at 100°. This gives 530 g (99.3% of theory) of a mixture of dinitroanthraquinones which has the following composition:

| 2,6-Dinitroanthraquinone | 0.46% |
|---|---|
| 2,7-Dinitroanthraquinone | 0.47% |
| 1,6-Dinitroanthraquinone | 11.0% |
| 1,7-Dinitroanthraquinone | 11.0% |
| 1,5-Dinitroanthraquinone | 37.8% (= 41.9% of theory)$^x$ |
| 1,8-Dinitroanthraquinone | 35.1% (= 39.3% of theory) |
| 1-Nitroanthraquinone | 1.31% |

$^x$Calculation: theoretical yield from Σanthraquinone and 1-nitroanthraquinone related to 1,5-dinitroanthraquinone and 1,8-dinitroanthraquinone formed (= total 1,5-dinitroanthraquinone and 1,8-dinitroanthraquinone to 1,5-dinitroanthraquinone and 1,8-dinitroanthraquinone employed).

EXAMPLE 10

208 g of anthraquinone are introduced, at 30°, in the course of ½ an hour, into a mixture of 424 g of 98% strength nitric acid and 500 g of sulphuric acid monohydrate, whilst stirring. A sample taken immediately after the end of the introduction and worked up still contained 4.75% of 1-nitroanthraquinone but no longer contained any anthraquinone. The mixture was then stirred for a further ½ hour at 40° (2.5% of 1-nitroanthraquinone) and for ½ an hour at 50° and introduced into 3,000 g of ice water and the product which had precipitated was filtered off, washed until neutral and dried. This gave 293 g (=98.3%) of a mixture of dinitroanthraquinones which which has the following composition:

| 2,6-Dinitroanthraquinone | 0.42% |
|---|---|
| 2,7-Dinitroanthraquinone | 0.44% |
| 1,6-Dinitroanthraquinone | 9.60% |
| 1,7-Dinitroanthraquinone | 9.44% |
| 1,5-Dinitroanthraquinone | 39.20% (= 38.5% of theory) |
| 1,8-Dinitroanthraquinone | 35.50% (= 34.9% of theory) |
| 1-Nitroanthraquinone | 1.56% |

EXAMPLE 11

208 g of anthraquinone are introduced, at 30°, in the course of 30 minutes, into a mixed acid consisting of 507 g of nitric acid (98% strength) and 418 g of sulphuric acid (91% strength) and the resulting mixture is stirred for a further A hours at B°. After the mixture has been stirred into 3,000 ml of ice water and the precipitate has been filtered off, washed until neutral and dried, 294 g (98.7%) of a mixture of dinitroanthraquinones which has the composition C are obtained:

| | | | | C. (in %) | | | | |
|---|---|---|---|---|---|---|---|---|
| A hrs. | B °C. | 1,5-Dinitro-anthraquinone | 1,8-Dinitro-anthraquinone | 1,6-Dinitro-anthranquinone | 1,7-Dinitro-anthraquinone | 2,6 + 2,7-Di-nitro-anthraquinone | 1 nitro-anthraquinone | 2 Anthra-quinone |
| 4 | 30 | 40.6 40.1% of | 37.0 36.5% of | 8.6 | 8.4 | 0.5 | 2.0 | — | — |

| A hrs. | B °C. | 1,5-Dinitro- anthraquinone | 1,8-Dinitro- anthraquinone | C. (in %) | | 2,6 + 2,7-Di- nitro- anthraquinone | 1 nitro- anthraquinone | 2 Anthra- quinone |
|---|---|---|---|---|---|---|---|---|
| | | | | 1,6-Dinitro- anthranquinone | 1,7-Dinitro- anthraquinone | | | |
| 0.5 | 45 | theory 40.2 39.7% of theory | theory 36.0 35.5% of theory | 9.1 | 8.9 | 0.6 | 1.9 | — — |
| 0.25 | 60 | 39.0 38.5% of theory | 35.2 34.7% of theory | 9.8 | 9.7 | 0.8 | 1.1 | — — |

EXAMPLE 12

A mixture of 72.6 g of anthraquinone, 56.7 g of the product obtained from the mother liquor from the pre-purification of 1-nitroanthraquinone and 34.1 g of the sump product which has been obtained from the distillation of 1-nitroanthraquinone and has the following composition: 48.3% of anthraquinone, 5.2% of 1,5-dinitroanthraquinone, 5.6% of 1,8-dinitroanthraquinone, 1.3% of 1,6-dinitroanthraquinone, 1.4% of 1,7-dinitroanthraquinone, 26.7% of 1-nitroanthraquinone, 9.9% of 2-nitroanthraquinone and 0.5% of 2,6- and 2,7-dinitroanthraquinone, are introduced, at 30°, in the course of 30 minutes, into a mixed acid consisting of 226 ml of nitric acid (98% strength) and 213 ml of sulphuric acid (85% strength).

The mixture is stirred for a further 1 hour at 30°, 1 hour at 40° and, finally, 2 hours at 50°. After the mixture has been stirred into 2,000 ml of water and the product which has precipitated has been filtered off, washed until neutral and dried, 207.5 g (99%) of a mixture of dinitroanthraquinones which has the following composition are obtained:
37.4% of 1,5-dinitroanthraquinone (41.7% of theory)*
35.9% of 1,8-dinitroanthraquinone (39.5% of theory)
10.3% of 1,6-dinitroanthraquinone
10.5% of 1,7-dinitroanthraquinone
2.1% of 1-nitroanthraquinone
1.0% of 2,6- and 2,7-dinitroanthraquinone.
Calculation: theoretical yield from Σanthraquinone and 1-nitroanthraquinone related to 1,5-dinitroanthraquinone and 1,8-dinitroanthraquinone formed (−total 1,5-dinitroanthraquinone and 1,8-dinitroanthraquinone −1,5-dinitroanthraquinone and 1,8-dinitroanthraquinone employed).

EXAMPLE 13

113 ml of nitric acid (100% strength) and 147 g of sulphuric acid (83% strength) are mixed and 70 g of anthraquinone are added, at 30°, in the course of 10 minutes, whilst stirring. The mixture is stirred for a further 30 minutes at 30°, 30 minutes at 40°, 3 hours at 50° and 1 hour at 60°. After the mixture has been stirred into 1,000 ml of water and the precipitate has been filtered off, washed until neutral and dried, 97 g (96.8%) of a mixture of dinitroanthraquinones which has the following composition are obtained:

ANALYSIS:
39.8% of 1,5-dinitroanthraquinone (38.5% of theory)
37.2% of 1,8-Dinitroanthraquinone (36.0% of theory)
9.2% of 1,6-dinitroanthraquinone
9.0% of 1,7-dinitroanthraquinone
0.6% of 2,6 and 2,7-dinitroanthraquinone
1.6% of 1-nitroanthraquinone During the reaction, the following intermediate values are determined by analysis for the 1-nitroanthraquinone content after 30 minutes (40°) 9.7%
after 30 minutes (50°) 6.5%
after 2 hours (50°) 2.9%
after 3 hours (50°) 2.4%

EXAMPLE 14

The procedure is as in Example 13 but an equal amount of 96% strength nitric acid is employed in place of 100% strength nitric acid and an equal amount of 89% strength sulphuric acid is employed in place of 83% strength sulphuric acid.

97.7 g (97.5%) of a mixture of dinitroanthraquinones which has the following composition are obtained:

ANALYSIS
40.1% of 1,5-dinitroanthraquinone (39.1% of theory)
37.9% of 1,8-dinitroanthraquinone (37.0% of theory)
9.1% of 1,6-dinitroanthraquinone
8.9% of 1,7-dinitroanthraquinone
0.8% of 1-nitroanthraquinone During the reaction the following intermediate values are determined for 1-nitroanthraquinone:
after 30 minutes at 40° 6.1%
after 30 minutes at 50° 2.8%
after 1 hour at 50° 1.5%
after 2 hours at 50° 1.1%

EXAMPLE 15

733 g of the product obtained from the mother liquor from the pre-purification of 1-nitroanthraquinone and 436 g of the sump product from the distillation of 1-nitroanthraquinone are introduced, as a mixture, at a uniform rate in the course of 30 minutes, at 30°, into 1,500 ml of nitric acid (98% strength) and 900 ml of anhydrous sulphuric acid and the resulting mixture is then stirred for a further 30 minutes at 50° and 30 minutes at 60°. After the mixture has been stirred into 1,000 ml of water, the precipitate has been filtered off and the precipitate has been washed until neutral and dried, 1,321 g (98.8%) of a mixture of dinitroanthraquinones which has the following composition are obtained:

ANALYSIS
36.6% of 1,5-dinitroanthraquinone (47.1% of theory)+
33.6% of 1,8-dinitroanthraquinone (43.0% of theory)
11.7% of 1,6-dinitroanthraquinone
11.5% of 1,7-dinitroanthraquinone
1.3% of 1-nitroanthraquinone 1.2% of 2,6 and 2,7-dinitroanthraquinone After 30 minutes at 50° the 1-nitroanthraquinone content is: 8.4%. The feed materials have the following composition:

|  | Product from the mother liquor | Sump product |
|---|---|---|
| Anthraquinone | 11.2% | — |
| 1,5-Dinitroanthraquinone | 3.4% | 20.5% |
| 1,8-Dinitroanthraquinone | 6.4% | 13.9% |
| 1,6-Dinitroanthraquinone | 4.0% | 0.5% |
| 1,7-Dinitroanthraquinone | 3.9% | 0.4% |
| 1-Nitroanthraquinone | 41.4% | 59.8% |
| 2-Nitroanthraquinone | 26.2% | 0.2% | xCalculation: theoretical yield from Σanthraquinone and 1-nitroanthraquinone related to 1,5-dinitroanthraquinone and 1,8-dinitroanthraquinone formed (= total 1,5 and 1,8-dinitroanthraquinone to 1,5-dinitroanthraquinone and 1,8-dinitroanthraquinone introduced).

EXAMPLE 16

116 g of anthraquinone are introduced, at 35°, in the course of 15 minutes, into a mixture of 215 g of 98% strength nitric acid and 241 g of 96% strength sulphuric acid, whilst stirring. After the end of the introduction, a sample is immediately worked up by introducing it into ice water and filtering off the precipitate, washing it until neutral and drying (analysis, see below). The mixture is then warmed to 55° and stirred at 55° for 1 hour. The mixture is then stirred into 1,500 g of ice water and the product which has precipitated is filtered off, washed until neutral and dried. This gives: 163.4 g (98.5%) of a mixture of dinitroanthraquinones which has the composition given below:

| Analysis | Sample after introduction | Reaction product |
|---|---|---|
| Anthraquinone | 3.11% | — |
| 1-Nitroanthraquinone | 7.84% | 1.01% |
| 2-Nitroanthraquinone | — | — |
| 2,6-Dinitroanthraquinone | 0.43% | 0.38% |
| 2,7-Dinitroanthraquinone | 0.36% | 0.38% |
| 1,6-Dinitroanthraquinone | 8.57% | 9.66% |
| 1,7-Dinitroanthraquinone | 8.63% | 9.60% |
| 1,5-Dinitroanthraquinone | 36.00% | 39.70% (39.1% of theory) |
| 1,8-Dinitroanthraquinone | 32.30% | 36.10% (35.6% of theory) |

What is claimed is:

1. In the process for the preparation of a mixture of a dinitroanthraquinones having an at least 73% content of 1,5- and 1,8-dinitroanthraquinone relative to anthraquinone and/or 1-nitroanthraquinone employed, wherein anthraquinone, 1-nitroanthraquinone, a mixture of anthraquinone and 1-nitroanthraquinone, or a 1-nitroanthraquinone, which contains impurities such as anthraquinone, 2-nitroanthraquinone, dinitroanthraquinone and which is obtained during the production of 1-nitroanthraquinone, are nitrated with nitric acid with heating, the improvement which comprises (a) adding said anthraquinone, 1-nitroanthraquinone, mixture of anthraquinone and 1-nitroanthraquinone, or said 1-nitroanthraquinone, containing impurities such as anthraquinone, 2-nitroanthraquinone, dinitroanthraquinones and obtained during the production of 1-nitroanthraquinone to a mixture of sulfuric acid and nitric acid having a weight ratio of $H_2SO_4$: $NHO_3$ from 0.75 to 2:1 calculated on the basis of 100% acids, at 20° to 50° C., so that the weight ratio of nitric acid to solids is 1.5 to 2.5:1, (b) maintaining the mixture at said 20° to 50° C. temperature until more than 50% of the anthraquinoid starting compounds are dinitrated, then (c) raising the reaction temperature to 50° to 70° C. so that the temperature is at least 5° C. higher than that in step (a), then maintaining the latter reaction temperature until anthraquinone and nitroanthraquinone have disappeared or can be detected only in insignificant amounts.

2. Process according to claim 1, characterized in that sulphuric acid is added in an amount by weight which is about 1.0 to about 1.5 times that of nitric acid.

3. Process according to claim 1, characterized in that nitric acid is added in about 1.7 to about 2.4 times the amount by weight, relative to anthraquinone, 1-nitroanthraquinone or a mixture of anthraquinone and 1-nitroanthraquinone.

4. Process according to claim 1, characterized in that sulphuric acid is added in the form of 85 to 100% strength by weight sulphuric acid.

5. Process according to claim 1, characterized in that sulphuric acid is added in the form of 96% strength by weight sulphuric acid.

6. Process according to claim 1, characterized in that nitric acid is used in the form of 96 to 100% strength by weight nitric acid.

7. Process according to claim 1, characterized in that nitric acid is used in the form of 98% strength by weight nitric acid.

8. A process of claim 1 wherein in step (a) the weight ratio of $H_2SO_4$:$HNO_3$ is 0.9 to 1.3:1, the temperature is 30° to 45° C., and the weight ratio of nitric acid to solids is from 1.7 to 2.2 to 1; in step (b) the mixture is maintained at 30° to 45° C. until at least 80% of the starting anthraquinoid materials are dinitrated; and in step (c) the temperature is raised to 50° to 65° C. so that the temperature is at least 10° C. higher than that in step (a).

* * * * *